United States Patent
Moulin et al.

(10) Patent No.: US 8,048,127 B2
(45) Date of Patent: Nov. 1, 2011

(54) BONE FIXING DEVICE

(75) Inventors: Jean-Pierre Moulin, Lyons (FR); Christophe Roy, Chatuzange le Goubet (FR); Alexis Faure, Nantes (FR); Jean-Patrick Rakover, Rouillon (FR); Simon Le Naelou, Bouguenais (FR); Philippe Vernet, Le Mans (FR); Christian Cistac, La Roche sur Yon (FR); Philippe Bacon, Ceson Sevigne (FR); Arnaud Blamoutier, Cesson-Sevigne (FR); Jean-Jacques Allioux, Coueron (FR); Jean-Pierre Atanasiu, Poitiers (FR); Henry-François Parent, Angers (FR); Gilles Gagna, Le Mans (FR)

(73) Assignee: Arthroplastie-Diffusion, Lyons (FR)

( * ) Notice: Subject to any disclaimer, the term of this patent is extended or adjusted under 35 U.S.C. 154(b) by 291 days.

(21) Appl. No.: 12/302,537

(22) PCT Filed: May 30, 2007

(86) PCT No.: PCT/FR2007/000893
§ 371 (c)(1), (2), (4) Date: Jul. 20, 2009

(87) PCT Pub. No.: WO2007/138190
PCT Pub. Date: Dec. 6, 2007

(65) Prior Publication Data
US 2009/0318973 A1 Dec. 24, 2009

(30) Foreign Application Priority Data
May 30, 2006 (FR) ..................................... 06 04803

(51) Int. Cl.
*A61B 17/70* (2006.01)

(52) U.S. Cl. ...................................................... 606/278
(58) Field of Classification Search .......... 606/246–279, 606/300, 301, 305–308, 319, 328; 411/354, 411/355; 403/395, 398, 400
See application file for complete search history.

(56) References Cited

U.S. PATENT DOCUMENTS
1,052,200 A * 2/1913 Adams .............................. 5/289
(Continued)

FOREIGN PATENT DOCUMENTS
DE 102004010844 A1 10/2005
(Continued)

*Primary Examiner* — Eduardo C Robert
*Assistant Examiner* — Stuart S Bray
(74) *Attorney, Agent, or Firm* — Porzio, Bromberg & Newman, P.C.

(57) ABSTRACT

The invention concerns a bone fixing device (1) for immobilizing a linking rod (2) designed to connect at least one bone fragment (3) to another, said device comprising: at least one anchoring means (4) designed to be fixed on or in said bone fragment (3); at least one receiving part (7), secured to said anchoring means (4), designed to receive at least part of said linking rod (2); locking means (8) designed to lock said part of the linking rod (2) within said receiving part (7). The invention is characterized in that said locking means comprise at least one solid element (8) having a longitudinal axis, said solid element including at least one inclined surface (9) capable, under the action of a thrust directed along the longitudinal axis of said solid element, of gradually wedging by friction said part of the linking rod (2) into said receiving part (7), until said part of the linking rod (2) is completely locked inside said receiving part (7). The invention also concerns an assembly comprising such a device and a linking rod.

12 Claims, 7 Drawing Sheets

U.S. PATENT DOCUMENTS

| | | | |
|---|---|---|---|
| 1,534,776 A * | 4/1925 | Eisinga | 411/354 |
| 1,546,495 A * | 7/1925 | Lathrop | 403/395 |
| 1,670,521 A * | 5/1928 | Ray | 403/395 |
| 1,778,350 A * | 10/1930 | Bosco | 403/398 |
| 1,815,098 A * | 7/1931 | Earhart | 411/355 |
| 1,933,825 A * | 11/1933 | Sloan | 602/37 |
| 2,034,266 A * | 3/1936 | Moore et al. | 411/354 |
| 2,461,648 A * | 2/1949 | Macleod | 52/520 |
| 2,743,657 A * | 5/1956 | Kriegbaum | 403/395 |
| 4,525,096 A * | 6/1985 | Green et al. | 403/49 |
| 4,846,615 A * | 7/1989 | Forsyth | 411/355 |
| 5,507,746 A * | 4/1996 | Lin | 606/264 |
| 5,535,982 A * | 7/1996 | Zayic | 249/213 |
| 5,630,816 A * | 5/1997 | Kambin | 606/252 |
| 5,676,665 A * | 10/1997 | Bryan | 606/252 |
| 5,800,434 A * | 9/1998 | Campbell, Jr. | 606/279 |
| 5,989,250 A * | 11/1999 | Wagner et al. | 606/250 |
| 5,997,539 A * | 12/1999 | Errico et al. | 606/278 |
| 6,193,436 B1 * | 2/2001 | Ellis | 403/331 |
| 6,520,464 B1 * | 2/2003 | Morrissey et al. | 248/222.52 |
| 6,783,526 B1 * | 8/2004 | Lin et al. | 606/250 |
| 6,905,106 B2 * | 6/2005 | Myers et al. | 249/191 |
| 7,141,051 B2 * | 11/2006 | Janowski et al. | 606/272 |
| 7,318,687 B2 * | 1/2008 | Appleyard et al. | 403/341 |
| 7,635,380 B2 * | 12/2009 | Zucherman et al. | 606/267 |
| 7,731,736 B2 * | 6/2010 | Guenther et al. | 606/273 |
| 7,909,855 B2 * | 3/2011 | Drewry et al. | 606/265 |
| 7,963,978 B2 * | 6/2011 | Winslow et al. | 606/246 |
| 2005/0203518 A1 | 9/2005 | Biedermann et al. | |
| 2005/0234451 A1* | 10/2005 | Markworth | 606/61 |
| 2005/0277924 A1* | 12/2005 | Roychowdhury | 606/61 |
| 2005/0277927 A1* | 12/2005 | Guenther et al. | 606/61 |
| 2007/0276375 A1* | 11/2007 | Rapp | 606/61 |

FOREIGN PATENT DOCUMENTS

| | | |
|---|---|---|
| EP | 1210914 A1 | 5/2002 |
| WO | 9632070 A2 | 10/1996 |
| WO | 9965415 A1 | 12/1999 |

* cited by examiner

BONE FIXING DEVICE

CROSS REFERENCE TO RELATED APPLICATION

This is a National Stage of International Application PCT/FR2007/000893, filed May 30, 2007, which claims the benefit of Application No. 0604803, filed in France on May 30, 2006, the disclosures of which Applications are incorporated by reference herein.

The present invention relates to a bone fixation device for reducing, stabilizing or fixing bones, and to an assembly comprising such a device and a connecting rod designed to connect several bones or bone fragments to each other.

Bone fixation devices may be internal, in the form of implants applied completely inside the body of the patient, or external, but with anchoring means fixed in the bones to be treated.

External fixation devices with bone anchoring include plugs or pins, screwed or passing through the bone or the bone fragment to be fixed. Connecting elements, such as a connecting rod for example, positioned outside the body make use of locking systems with screw tightening such as nuts or screws. Such devices are tedious to employ due to their complexity. In addition they are tricky to adjust. Thus, when screwing the connecting rod, jolts may occur and create a gap at the anchoring site in the bone, weakening the fixation.

Internal fixation devices or again implants may take the form of nails or pins positioned longitudinally inside the bone or bone fragments to be fixed. However, such devices only enable treatment of long bones.

Implants may also exhibit the form of plates pierced by orifices accepting screws for fixing to the bone. However, such devices do not make it easy to align and/or position bones or bone fragments: this is because their position is dictated by that of the orifices.

Implants may alternatively exhibit the form of anchor points connected by bars, rods or plates located inside the patient. However, the employment and in situ assembly of this type of internal fixation device are complex and not quick.

There is therefore a need for external or internal fixation devices that are easy to employ quickly, while being reliable and ensuring optimal fixation.

The present invention aims to meet this need by proposing a fixation device which can be used as an external or internal fixation device, is particularly simple to apply and ensures excellent fixation.

The present invention relates to a bone fixation device capable of immobilizing a connecting rod designed to connect at least one bone fragment to another, said device comprising:
- at least one anchoring means intended to be fixed on or in said bone fragment;
- at least one receiving part, joined to said anchoring means, intended to receive at least one part of said connecting rod;
- locking means arranged to lock said part of said connecting rod within said receiving part;

characterized in that said locking means comprise at least one solid element having a longitudinal axis, said solid element comprising at least one inclined surface capable, under a push action directed along the longitudinal axis of said solid element, of creating by friction gradual wedging of said part of the connecting rod in said receiving part, through to complete locking of said part of the connecting rod in said receiving part.

The device according to the invention enables particularly simple and reliable locking of the connecting rod. In particular, the device according to the invention enables elimination of the screwing step necessary with devices of the prior art.

By virtue of the inclined surface of its locking means, the device according to the invention may be employed by simply pushing along the longitudinal axis of its locking means. The wedging of the connecting rod occurs gradually, smoothly, without jolts. Destabilization of the anchoring means at the bone or bone fragment being considered is thus avoided. No gap is created at the anchoring of the device in or on the bone or bone fragments. The fixation is thus ensured in a more reliable manner than with the devices of the prior art.

In one embodiment of the invention:
- said receiving part is U-shaped, said part of the connecting rod being received at the bottom of the U, the wall of each branch of the U being provided with an orifice;
- said solid element is in the form of a wedge, the cross section of which increases from a first end, called the thin end, to a second end, called the wide end, the diameter of the circle in which the cross section of said wide end is inscribed being strictly wider than the diameter of the circle inscribed in said orifice;
- said wedge being able to be inserted by its thin end successively into the orifices of the walls of the branches of the U of said receiving part, perpendicular to said connecting rod, and to be pushed along its longitudinal axis until coming into contact with said connecting rod and creating friction between said connecting rod and the bottom of the receiving part;
- such that in the locking position, said wedge passes through each orifice of each branch of the U of said receiving part and keeps said part of the connecting rod locked against the bottom of said receiving part.

The perimeter of the cross section of said wedge preferably has a shape chosen from a circle, a polygon, or a combination of arcs of circle and/or segments.

In one embodiment of the invention, said wedge has, on its part intended to be in contact with said connecting rod in the locked position, recessed or raised structures, such as bumps, grooves and/or helices, capable of securing the locking of said connecting rod within said receiving part.

The locking means are preferably joined to said device. The device according to the invention can thus be provided ready for use, with its locking means already installed. Such a device allows time to be saved by the surgeon, who only has to push on the locking means, for example the wedge, already present on the device, in order to fix the connecting rod. The fixation operation is thus made much easier and may be carried out extremely quickly.

In one embodiment of the invention, said wedge has, below its thin end, a longitudinal channel extending through to its wide end which is able to cooperate with a lug provided in the orifice of the wall of a first branch of the U in order to allow movement of said wedge toward the orifice in the wall of the second branch of the U, and to prevent complete return of said wedge toward the orifice in the wall of the first branch of the U and hence its separation from said device.

In one embodiment of the invention, in a configuration said to be "mobile", said receiving part is hinged on said anchoring means so as to allow a controllable angular orientation in the three directions between said anchoring means and said connecting rod.

In one embodiment of the invention, said receiving part has a conical bottom pierced by an axial hole,
- said anchoring means is in the form of a screw comprising a spherical head of a diameter strictly greater than the diameter of said axial hole, said spherical head being engaged in the conical bottom.

Advantageously, said conical bottom forms a cone angle α between 15° and 60°. Such an angle allows an increase in the tightening of the screw when pressure is applied. It also allows reversibility of the locking. The surgeon can easily loosen the locking means and orient the screw and hence the connecting rod differently.

In one embodiment of the invention, said branches of the U are able to bend between an unbent rest position and a bent position under stress, in order to allow the connecting rod, under stress, to pass toward the bottom of the receiving part, and to prevent, at rest, said connecting rod from leaving the bottom of the receiving part.

In one embodiment of the invention, said anchoring means is in the form of an elongate screw and the longitudinal axis of the U of said receiving part is approximately parallel to, and preferably coincides with, the longitudinal axis A of said elongate screw.

In another embodiment of the invention, said anchoring means is in the form of an elongate screw and the longitudinal axis of the U of said receiving part is approximately perpendicular to the longitudinal axis A of said elongate screw.

The present invention also relates to a bone fixation assembly, characterized in that it comprises at least one device such as described above and a connecting rod.

In one embodiment of the invention, said connecting rod has a cross section approximately in the shape of a crescent, said rod being shaped. Such a rod is preferably peroperatively shaped in order to match its shape to the morphology of the patient.

In another embodiment of the invention, said connecting rod is straight and has a cross section in the shape of a polygon.

The advantages of the present invention will now emerge from the description below, accompanied by the appended drawings, in which.

Figure 1:
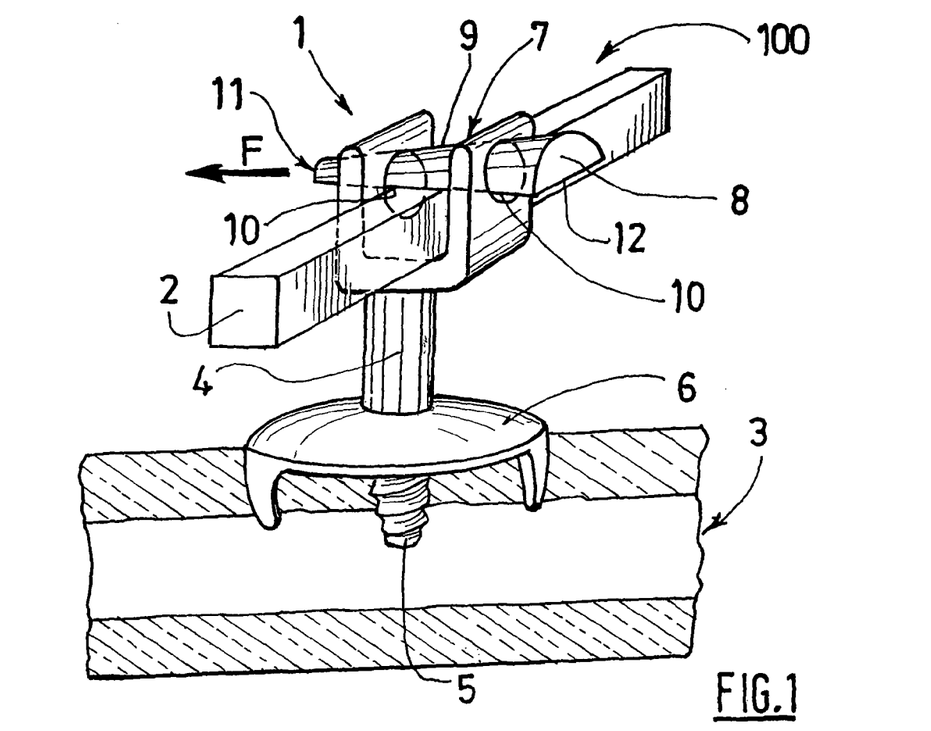
FIG. 1 is a perspective view of a bone fixation device according to the invention in the locked position.

FIG. 1 shows an assembly 100 according to the invention comprising a device 1 according to the invention to immobilize a connecting rod 2 intended to connect several bones or bone fragments 3 to each other. For example, this connecting rod 2 may connect two vertebrae to each other or else several bone segments, segments of the same bone for example (see FIG. 12).

The device 1 of FIG. 1 comprises an anchoring means in the form of an anchoring screw 4, the threaded end 5 of which is fixed, for example by screwing, into the bone 3. In the example of FIG. 1, a fixation means in the form of a platform 6 provided with claws anchoring themselves in the bone 3 is also present, in order to reinforce the anchoring of the device 1 in the bone 3.

The device of FIG. 1 also comprises a receiving part 7, joined to the anchoring means 4, this receiving part receiving at least a part of the connecting rod 2. In the example shown, the receiving part 7 is U-shaped, the wall of each branch of the U being provided with an orifice 10. The two orifices 10 are preferably identical. The connecting rod 2 is received at the bottom of the U. In the example shown, the longitudinal axis of the U coincides with the longitudinal axis of the anchoring screw 4.

The device according to the invention of FIG. 1 is in the locked position: thus, the connecting rod 2 is locked within the receiving part 7 by locking means. In the example shown, these locking means comprise a solid element in the form of a wedge 8, with a noticeably elongate shape and having an inclined surface 9, directed approximately along the longitudinal axis of the wedge 8. Due to its inclined surface 9, the wedge 8 has a variable cross section which increases from one of its ends to the other. The smallest cross-section end 11 will be called the thin end, and the larger cross-section end 12 will be called the wide end. The diameter of the circle in which the cross section of the wide end 12 of the wedge 8 is inscribed is strictly greater than the diameter of the circle inscribed in the orifice 10.

In the example shown in FIG. 1, the perimeter of the cross section of the wedge 8 has the shape of a combination of a semi-circle and a segment, the wedge 8 having approximately the shape of a half-portion of a cone.

As emerges from FIG. 1, the application of the wedge 8 and the locking of the connecting rod 2 is carried out in the following way: the device 1 is given to the surgeon in an open position, for example without the wedge 8. The surgeon places the connecting rod 2 at the bottom of the U of the receiving part 7, then he inserts the wedge 8 into a first orifice 10 by the thin end 11 of the wedge 8, perpendicular to the connecting rod 2, according to the arrow F shown in FIG. 1. The surgeon then pushes on the wide end 12 of the wedge 8, along the longitudinal axis of the wedge, and the thin end 11 of the wedge passes through the second orifice 10. In the course of its movement according to the arrow F, the wedge 8 comes into contact with the connecting rod 2 and creates friction between the connecting rod 2 and the bottom of the receiving part 7. As it advances in the direction of the arrow F, the inclined surface 9 of the wedge 8 creates a gradual wedging of the connecting rod 2 in the receiving part 7. At the end of the operation, the surgeon, possibly using a tightening device, firmly tightens the wedge 8 and the connecting rod 2 is completely locked within the receiving part.

Thus, due to the lack of screwing the locking means, the operation of applying the wedge 8 and of locking the connecting rod 2 is carried out gently, gradually, and without jolts. There is thus no risk of causing a jolt at the anchoring means, here the screw 4, and of creating a gap in the bone that would then destabilize the fixing of the device and therefore of the connecting rod 2.

Figure 2:
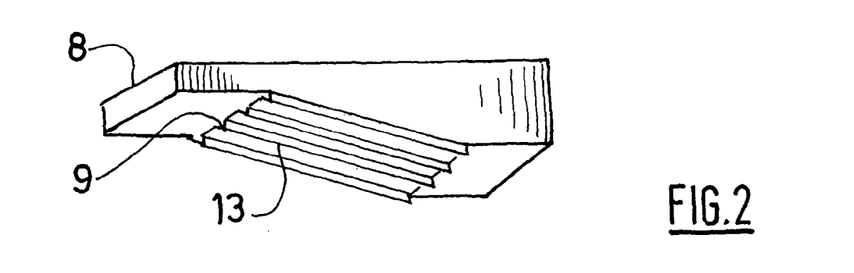
FIG. 2 is a perspective view of a locking means of a device according to the invention.

FIG. 2 shows a wedge 8, the perimeter of the cross section of which is a polygon in the form of a rectangle. The wedge 8 of FIG. 2 furthermore has longitudinal grooves 13, intended to be in contact with the connecting rod 2, on its inclined surface 9. These longitudinal grooves are capable of securing the locking of the connecting rod 2 within the receiving part 7.

Figure 3:
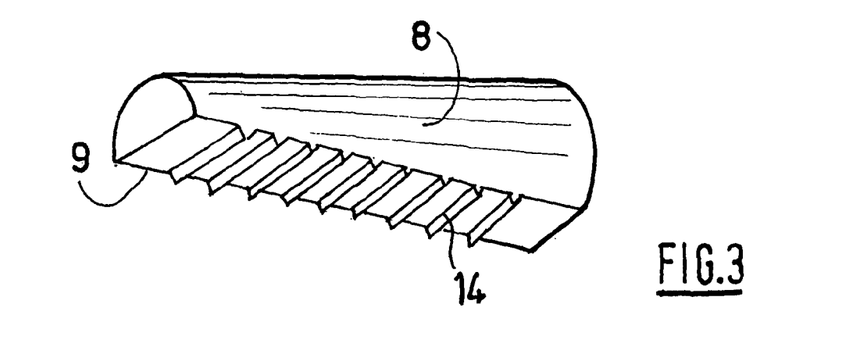
FIG. 3 is a perspective view of a variant of a locking means of a device according to the invention.

FIG. 3 shows a variant of the wedge 8 of FIG. 2, the inclined surface 9 of which, intended to be in contact with the connecting rod 2, comprises transverse grooves 14. These grooves 14 increase the force locking the connecting rod 2 in the receiving part 7.

Figure 4:
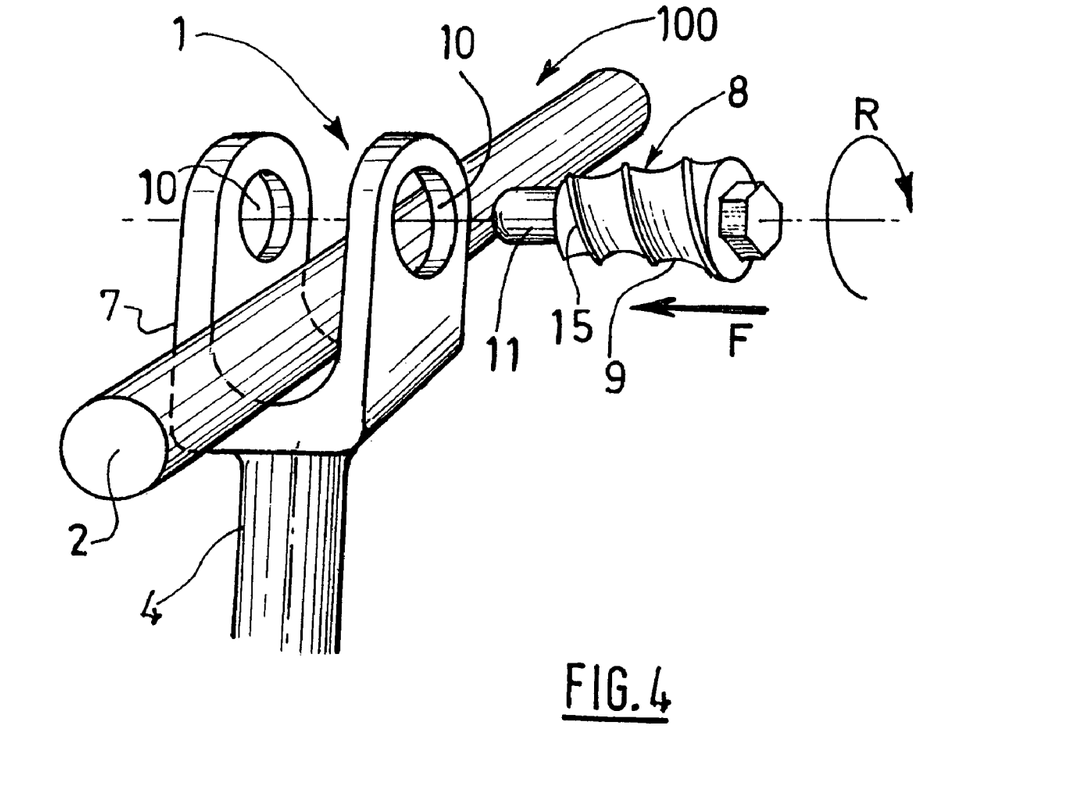
FIG. 4 is a perspective view of another variant of a locking means of a device according to the invention.

FIG. 4 partly shows a device 1 according to the invention, equipped with a wedge 8, the inclined surface 9 of which has a helix 15. According to the example of this figure, the surgeon, after having placed the connecting rod 2 at the bottom of the receiving part 7, inserts the wedge 8 successively through the two orifices 10 by the thin end 11 of said wedge 8 by pushing the latter along its longitudinal axis, i.e. along the arrow F shown in this figure. At the same time as this translation movement, the surgeon gives the wedge 8 a rotational movement according to the arrow R shown in this figure. Through this movement, the helix 15 cooperates with the orifices 10 and ensures better final locking of the connecting rod 2 in the receiving part 7.

Figures 6, 7:
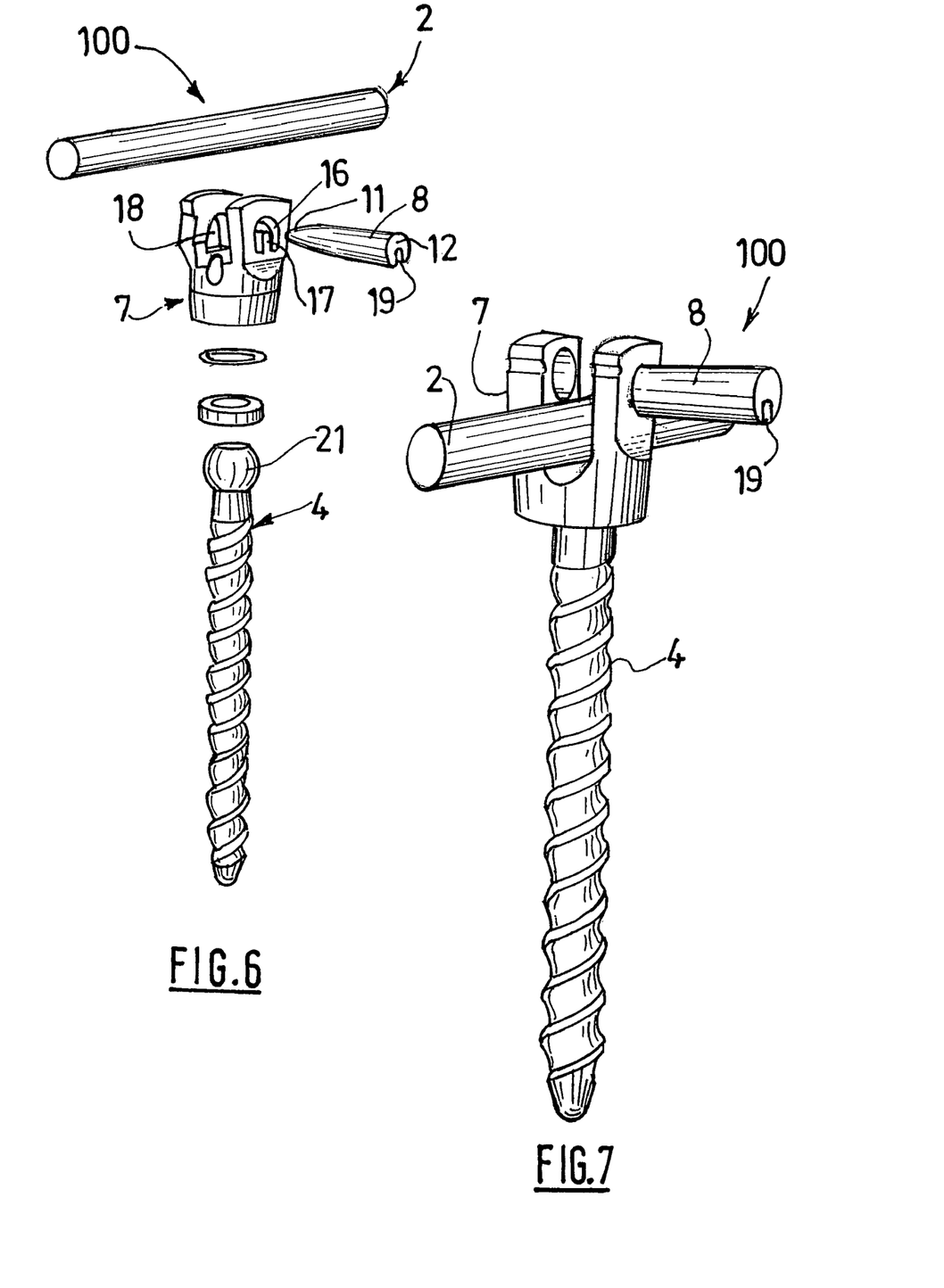
FIG. 6 is an exploded perspective view of a variant of a device according to the invention.
FIG. 7 is a perspective view of the device according to FIG. 6 in the open position.
Figures 8, 10:
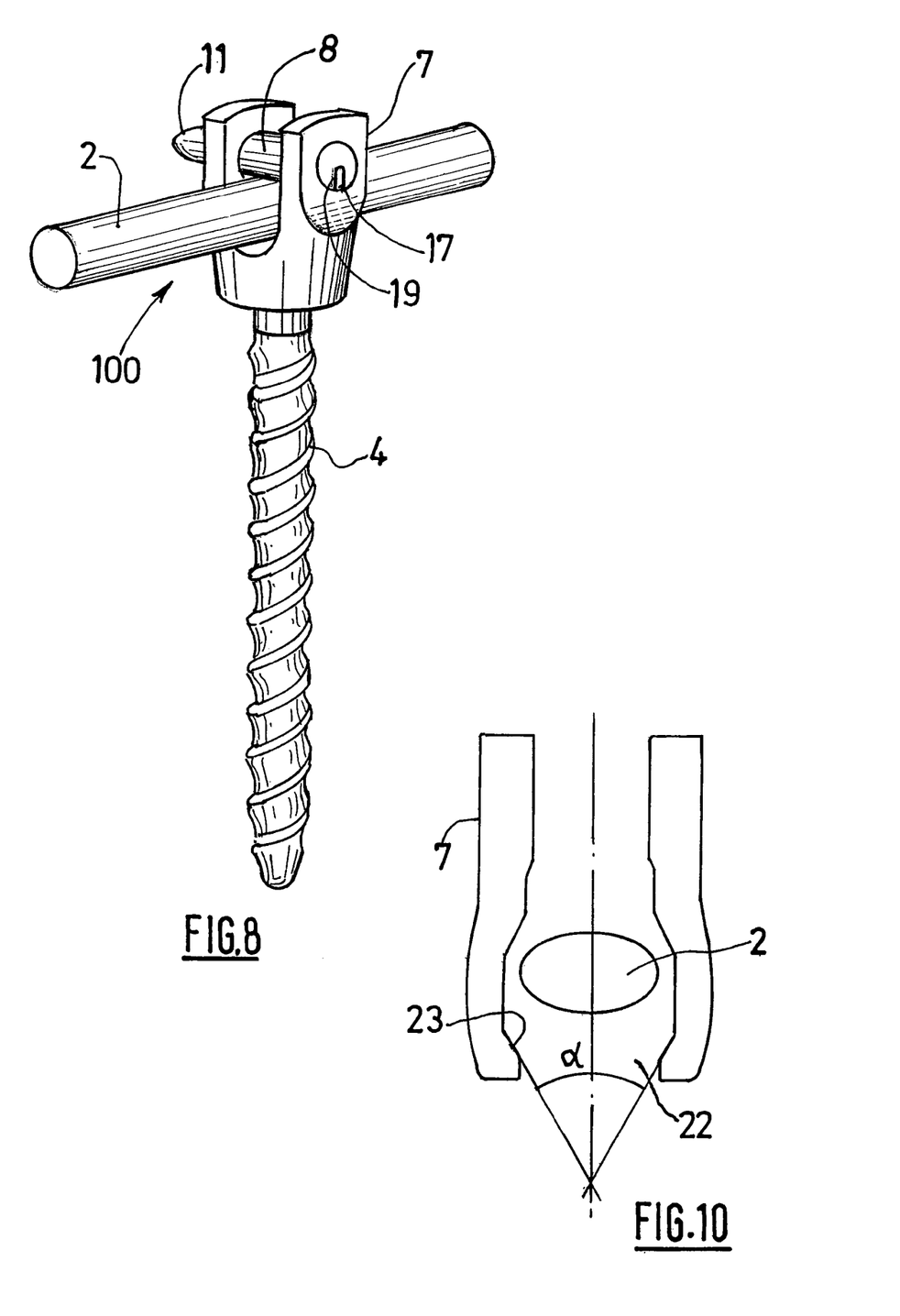
FIG. 8 is a perspective view of the device according to FIG. 6 in the locked position.
FIG. 10 is a cutaway view of the receiving part of the device according to FIG. 9.

FIGS. 6 to 8 show a variant of the device 1 according to the invention, in exploded perspective, in an open position and in a closed position respectively. In the example shown in these figures, the locking means are joined to the device. Such an embodiment enables the surgeon to apply the device according to the invention more quickly than with devices of the prior art. This is because, according to the invention, the locking means is part of the device and the surgeon only manipulates a single tool.

Figure 5:
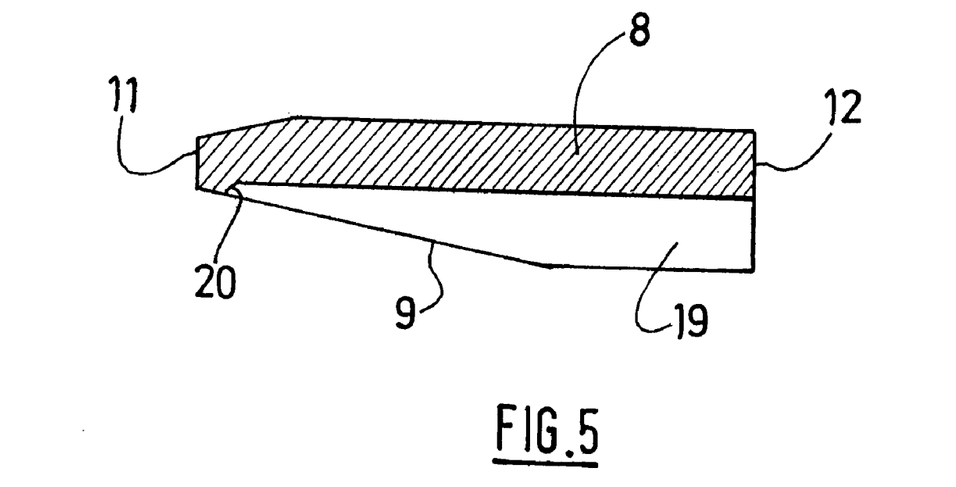
FIG. 5 is a cutaway view of the locking means of the device according to FIGS. 6 to 8.

As is apparent in FIG. 6, the receiving part 7 comprises, on the wall of one of its branches of the U, a first orifice 16 in the shape of a half disk, the base of the half disk being provided with a lug 17. It comprises, on the wall of the second branch of the U, a second orifice 18 in the shape of a half disk, this second orifice 18 not including a lug. As is more clearly apparent from FIG. 5 and FIG. 6, the wedge 8 comprises, below its thin end 11, a longitudinal channel 19 extending through to its wide end 12. The start of the longitudinal channel 19 below the thin end 11 of the wedge 8 defines a retainer 20 that comes to rest against the lug 17 when the wedge 8 is in the open position, as shown in FIG. 7.

Thus the longitudinal channel 19 of the wedge 8 cooperates with the lug 17 in the orifice 16 of the wall of the first branch of the U so as to allow displacement of the wedge 8 toward the orifice 18 of the second branch of the U, so as to be able to effect the locking of the connecting rod 2, as shown in FIG. 8, while preventing complete return of said wedge 8 toward the orifice of the wall of the first branch of the U and thus its separation from said device 1, in particular in the open position, as shown in FIG. 7.

Figure 9:
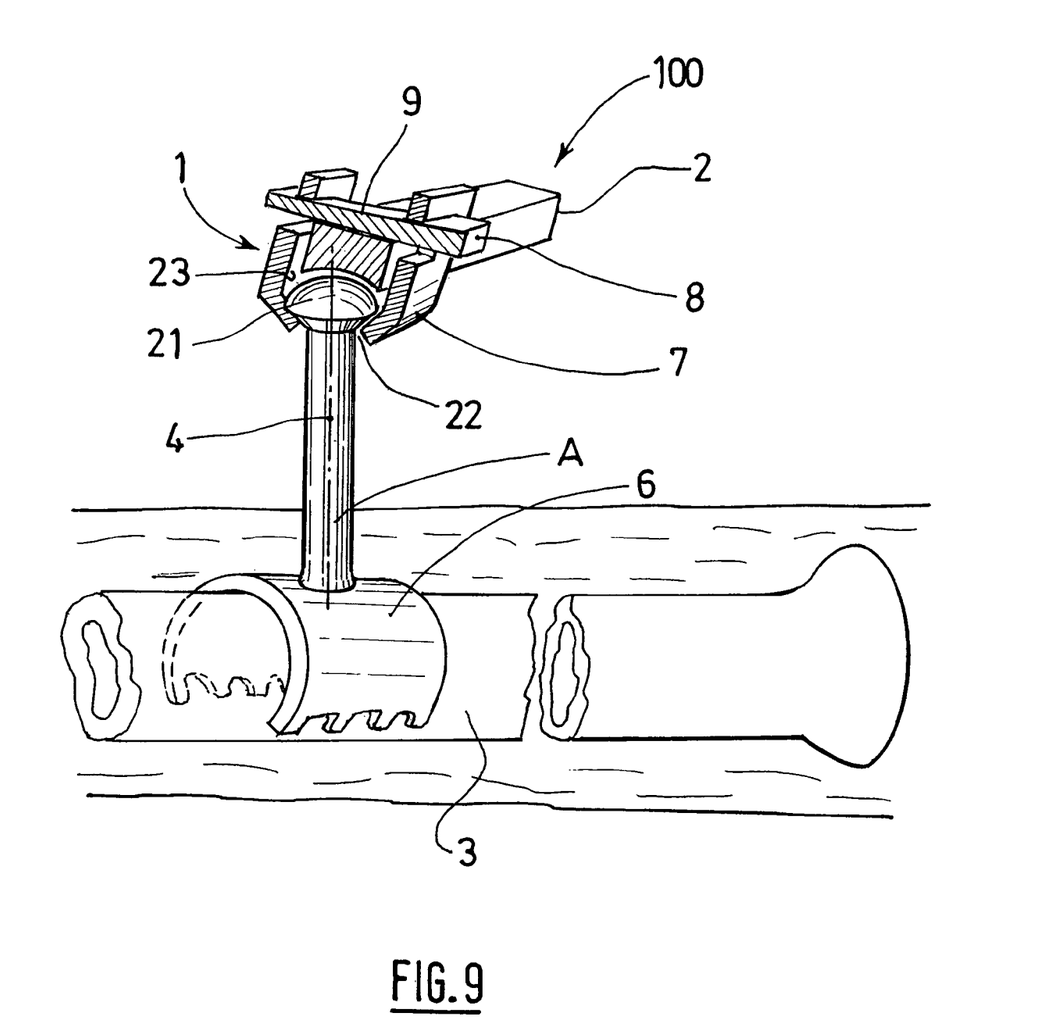
FIG. 9 is a perspective view of another variant of a device according to the invention.

The device 1 of FIGS. 6 to 8 and the device 1 of FIG. 9 furthermore comprise a receiving part 7 which is hinged on the anchoring means, namely the screw 4. As is apparent from FIG. 6, the screw 4 comprises a spherical head 21. The bottom 23 of the receiving part 7 is conical and comprises an axial hole 22, visible in FIGS. 9 and 10. A cutaway view of the receiving part 7 of the devices of FIGS. 6 to 9 is shown in FIG. 10.

The spherical head 21 has a diameter strictly greater than the diameter of the axial hole 22. In the example shown in FIG. 10, the bottom 23 of the receiving part 7 forms a cone angle α of between 15° and 60°, preferably around 500. This spherical head 21 is engaged in the conical bottom 23 of the receiving part, as shown in FIG. 9.

Thus in a mobile configuration, as shown in FIG. 9, the receiving part 7 is hinged on the anchoring screw 4, so as to allow a controllable angular orientation in the three directions between the anchoring screw 4 and the connecting rod 2.

The surgeon can thus choose the orientation of the connecting rod 2 very precisely before tightening the wedge 8 so as to lock said connecting rod 2. In particular, by virtue of the gradual and gentle wedging made possible by the inclined surface 9 of the locking means of the device 1 according to the invention, the locking is reversible and the surgeon can easily loosen the wedge 8, for example in order to adjust the orientation of the connecting rod 2, then re-tighten this wedge 8, and do this without jolts to the anchoring screw 4 and therefore at the anchoring of the device 1 on the bone or bone fragment 3.

In addition, the branches of the U of the receiving part 7 are preferably able to bend between an unbent rest position and a bent position under stress. These branches thus allow the connecting rod 2, under stress, to pass toward the bottom 23 of the receiving part 7, but they prevent, at rest, said connecting rod 2 from leaving the bottom 23 of the receiving part 7, as shown in FIG. 10.

In FIG. 9 the anchoring means 4 comprises a means 6 of fixation to the bone fragment 3 in the form of a half-collar surrounding the bone fragment 3.

Figure 11:
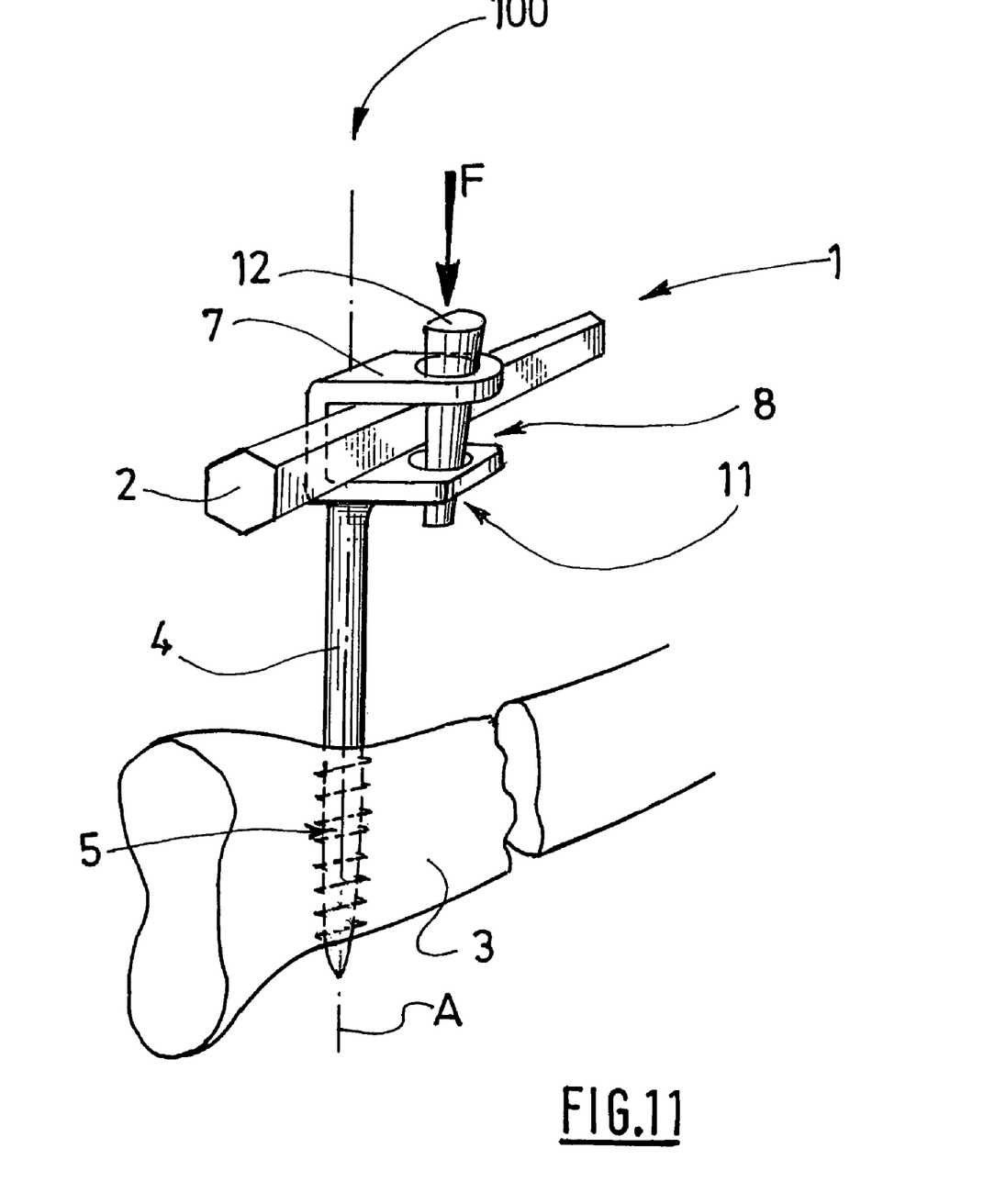
FIG. 11 is a perspective view of another variant of a device according to the invention.

FIG. 11 shows a variant of a device 1 according to the invention, in which the longitudinal axis of the U of the receiving part 7 is perpendicular to the longitudinal axis A of the anchoring screw 4. In this case, the longitudinal axis of the wedge 8 is parallel to the longitudinal axis A of the anchoring screw 4 and the connecting rod 2 is inserted into the receiving part 7 perpendicular to the longitudinal axis A of the anchoring screw 4. This device 1 operates in the same way as that of FIG. 1.

Figure 12:
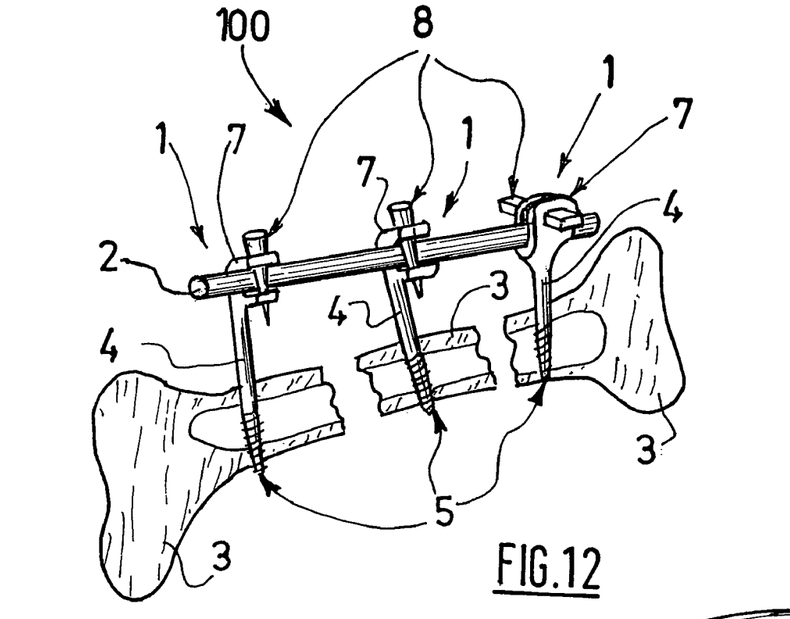
FIG. 12 is a perspective view of the fixation of three bone fragments using three devices according to the invention.

FIG. 12 shows the fixation of three bone fragments 3 using an assembly 100 according to the invention comprising three devices 1 according to the present invention and a connecting rod 2. By virtue of the devices 1, the connecting rod 2 is kept firmly locked in the orientation desired by the surgeon. It is thus possible, for example, to reduce the bone fractures shown by rejoining its various fragments.

The device according to the invention is particularly advantageous in the case in which the operation to reduce the fracture of a bone makes it necessary, as in the example of FIG. 12, to apply three devices. The ease and the speed of application of the devices according to the invention allows the time of surgical intervention, and hence the associated risks, to be reduced, and the trauma of the patient to be minimized.

Figure 13:
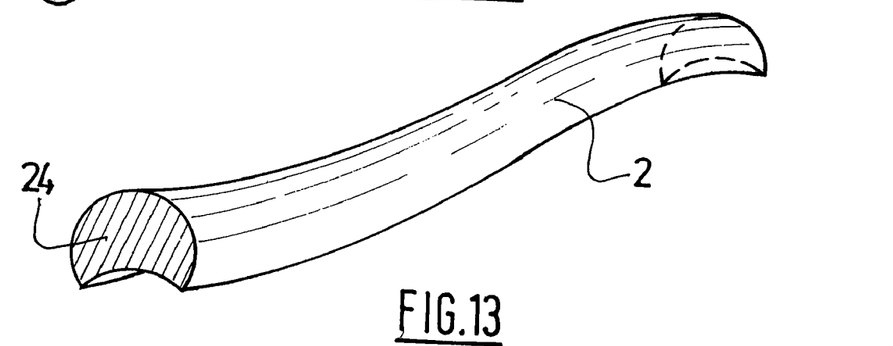
FIG. 13 is a perspective view of a connecting rod of an assembly according to the invention.
Figure 14:
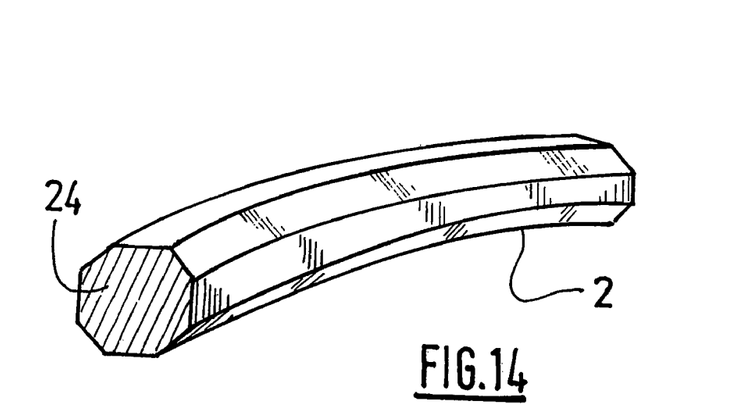
FIG. 14 is a variant of the connecting rod of FIG. 13.

FIGS. 13 and 14 show connecting rods 2 suitable for the devices 1 and for the assemblies 100 according to the invention.

FIG. 13 shows a connecting rod 2 having a cross section 24 that is approximately in the shape of a crescent, said rod 2 being shaped. Such a rod 2 is preferably peroperatively shaped in order to match its shape to the morphology of the patient.

FIG. 14 shows a connecting rod 2 that is straight and has a cross section 24 in the shape of a polygon.

The device 1 according to the invention may be used to join to each other two or more small short bones, such as the bones of the wrists, ankles, or the vertebral column, such as the vertebrae, or alternatively to immobilize several fragments of a long bone or several bones to each other. Its application is particularly simple, quick and reliable. In particular, the device 1 according to the invention enables gradual and reversible locking of the connecting rod 2, without jolts and without the risk of destabilizing the anchoring means of the device 1 at the bone or bone fragments to be connected to each other.

The device and the assembly according to the invention may equally well be used as internal fixation devices, as implants inside the body of the patient, and as external fixation devices, the head of the anchoring screw being fixed in the bone or the bone fragment and the receiving part being outside the body of the patient.

The invention claimed is:

1. A bone fixation device capable of immobilizing a connecting rod designed to connect at least one bone fragment to another, said device comprising:
    at least one anchoring means intended to be fixed on or in said bone fragment;
    at least one receiving part, joined to said anchoring means, intended to receive at least one part of said connecting rod;
    locking means arranged to lock said part of said connecting rod within said receiving part;
    characterized in that said locking means comprise at least one solid element having a longitudinal axis, said solid element comprising at least one inclined surface capable, under a push action directed along the longitudinal axis of said solid element, of creating by friction gradual wedging of said part of the connecting rod in said receiving part, through to complete locking of said part of the connecting rod in said receiving part;
    said receiving part being U-shaped, said part of the connecting rod being received at the bottom of the U, the wall of each branch of the U being provided with an orifice;
    said solid element being in the form of a wedge, the cross section of which increases from a first end, called the thin end, to a second end, called the wide end, the diameter of the circle in which the cross section of said wide end is inscribed being strictly wider than the diameter of the circle inscribed in said orifice;
    said wedge being able to be inserted by its thin end successively into the orifices of the walls of the branches of the U of said receiving part, perpendicular to said connecting rod, and to be pushed along its longitudinal axis until coming into contact with said connecting rod and creating friction between said connecting rod and the bottom of the receiving part;
    such that in the locking position, said wedge passes through each orifice of each branch of the U of said receiving part and keeps said part of the connecting rod locked against the bottom of said receiving part, said locking means being joined to said device, said wedge having, below its thin end, a longitudinal channel extending through to its wide end which is able to cooperate with a lug provided in the orifice of the wall of a first branch of the U in order to allow movement of said wedge toward the orifice in the wall of the second branch of the U, and to prevent complete return of said wedge toward the orifice in the wall of the first branch of the U and hence separation of the latter from said device.

2. The device as claimed claim 1, characterized in that the perimeter of the cross section of said wedge has a shape chosen from a circle, a polygon, or a combination of arcs of circle and/or segments.

3. The device as claimed in claim 1, characterized in that said wedge has, on its part intended to be in contact with said connecting rod in the locked position, recessed or raised structures, such as bumps, grooves and/or helices, capable of securing the locking of said connecting rod within said receiving part.

4. The device as claimed in claim 1, characterized in that in a configuration said to be "mobile", said receiving part is hinged on said anchoring means so as to allow a controllable angular orientation in the three directions between said anchoring means and said connecting rod.

5. The device as claimed claim 4, characterized in that said receiving part has a conical bottom pierced by an axial hole,
    said anchoring means is in the form of a screw comprising a spherical head of a diameter strictly greater than the diameter of said axial hole, said spherical head being engaged in the conical bottom.

6. The device as claimed claim 5, characterized in that said conical bottom forms a cone angle α between 15° and 60°.

7. The device as claimed in claim 1, characterized in that said branches of the U are able to bend between an unbent rest position and a bent position under stress, in order to allow the connecting rod, under stress, to pass toward the bottom of the receiving part, and to prevent, at rest, said connecting rod from leaving the bottom of the receiving part.

8. The device as claimed in claim 1, characterized in that, said anchoring means being in the form of an elongate screw, the longitudinal axis of the U of said receiving part is approximately parallel to, and preferably coincides with, the longitudinal axis A of said elongate screw.

9. The device as claimed in claim 1, characterized in that, said anchoring means being in the form of an elongate screw, the longitudinal axis of the U of said receiving part is approximately perpendicular to the longitudinal axis A of said elongate screw.

10. A bone fixation assembly, characterized in that it comprises at least one device as claimed in claim 1 and a connecting rod.

11. An assembly as claimed in claim 10, characterized in that said connecting rod has a cross section approximately in the shape of a crescent, said rod being shaped.

12. An assembly as claimed in claim 10, characterized in that said connecting rod is straight and has a cross section in the shape of a polygon.

* * * * *